United States Patent [19]
Frieze et al.

[11] Patent Number: 5,766,561
[45] Date of Patent: Jun. 16, 1998

[54] STERILIZABLE SILICONE MAT APPARATUS

[75] Inventors: Marcia A. Frieze, Alpine; Kate Kislevitz, Tenafly, both of N.J.

[73] Assignee: Case Medical, Inc., Ridgefield, N.J.

[21] Appl. No.: 838,930

[22] Filed: Apr. 23, 1997

[51] Int. Cl.$^6$ ............................................. A61L 2/00
[52] U.S. Cl. .................... 422/297; 422/297; 422/300; 211/70.6; 206/370; 206/438; 206/765
[58] Field of Search ........................ 422/300, 297; 211/70.6; 206/438, 439, 370, 765

[56] References Cited

U.S. PATENT DOCUMENTS

| | | | |
|---|---|---|---|
| 4,798,292 | 1/1989 | Hauze | 206/439 |
| 5,098,676 | 3/1992 | Brooks, Jr. | 422/292 |
| 5,211,915 | 5/1993 | Monch | 422/102 |
| 5,279,800 | 1/1994 | Berry, Jr. | 422/300 |
| 5,340,551 | 8/1994 | Berry, Jr. | 422/300 |
| 5,407,648 | 4/1995 | Allen et al. | 422/297 |

*Primary Examiner*—Robert J. Warden
*Assistant Examiner*—Fariborz Moazzam
*Attorney, Agent, or Firm*—Woodbridge & Associates

[57] ABSTRACT

A sterilizable silicone mat (10) includes a repeating S shaped rib structure (38) on the bottom surface (28) that aligns the mat (10) with steam apertures (20) in a support tray (12) and facilitates maximum steam penetration and optimum water drainage while reducing condensate. The mat body (26) includes a top surface (24) and a bottom surface (28) and a plurality of steam penetration holes or apertures (40). Each steam penetration hole (40) is surrounded by four instrument supporting finger-like structures (30) located on the top surface (24) of the mat (10). The four fingers (30) that surround each steam penetration hole (40) are located at 90 degrees with respect to each other. A plurality of S shaped rib structures (38) are located on the bottom surface (28) of the mat (10). Each S shaped rib (38) separates two adjacent steam holes (46) and includes a nub (42) at the distal ends of each S shaped rib (38) for engaging some of the steam penetration holes (20) in the bottom (18) of the tray (12). The nubs (42) insure that the steam penetration holes (20) in the tray (12) align directly opposite the steam penetration holes (40) in the mat body (26). The holes (40), fingers (30) and associated S shaped rib structures (38) are organized into subgroups (48) separated by long, straight continuous land sections (50) so that the mat (10) can by cut and subdivided into smaller mats depending upon the size of the sterilizable tray (12) to be used.

8 Claims, 5 Drawing Sheets

STERILIZABLE SILICONE MAT APPARATUS

BACKGROUND OF THE INVENTION

1. Field of the Invention

The invention relates, in general, to a silicone mat employed with a tray to sterilize medical instruments with steam and, in particular, to a sterilizable silicone mat that includes a support system on its bottom surface that permits maximum steam penetration and water drainage while reducing condensation.

2. Description of Related Art

There are several known techniques for holding medical instruments in sterilizable trays.

One of the most common techniques is to permanently attach brackets to the bottom of the tray. The brackets have notches for holding specific tools or instruments. Unfortunately such devices tend to be custom made for the ultimate user and therefor expensive to manufacture and limited in their flexibility.

Another approach is to use a flexible resilient mat with raised projections or fingers thereon to keep the instruments from sliding. Disclosures of such devices are found in the following U.S. Pat. Nos.: 5,098,676; 5,279,800 (FIG. 3); 5,340,551 (FIG. 3); 5,211,915; and, 5,407,648 among others. While such inventions may be improvements over prior mat structures, nevertheless, they frequently have drawbacks too. In particular, they tend to slide inside the tray and the distribution of sterilizable steam inside the tray can be uneven thereby preventing optimum drainage, inhibiting maximum steam penetration and increasing undesirable condensate.

It was in the context of the forgoing prior art that the present invention arose.

SUMMARY OF THE INVENTION

Briefly described, the invention comprises a mat that fits within a sterilizable tray. The mat has fingers or projections on its top surface for supporting medical instruments. The bottom surface has a plurality of S shaped ribs that allow the mat to float over the bottom of the tray. Each of the S shaped ribs has a pair of nubs located at opposite ends of the S shaped rib. The nubs align with, and are received in, some of the steam holes in the bottom of the tray. Steam penetration holes are also located in the body of the mat and are each surrounded by four fingers arranged in a square pattern 90 degrees with respect to each other. The S shaped ribs separate adjacent steam penetration holes in the mat body. When the nubs are properly seated in the steam holes in the floor or bottom of the tray, the remaining steam holes in the floor are perfectly aligned with the corresponding steam penetration holes in the mat body. This structure allows for optimum water drainage, maximum steam penetration and greater condensate reduction.

The steam penetration holes in the mat can also be divided into two or more square or rectangular subgroups separated by relatively long and straight land areas so that the mat can be conveniently cut up to fit into smaller trays.

These and other features of the invention may be more fully understood by reference to the following drawings.

DETAILED DESCRIPTION OF THE INVENTION

During the course of this description like numbers will be used to identify like elements accordingly to the different figures that illustrate the invention.

Figure 1:
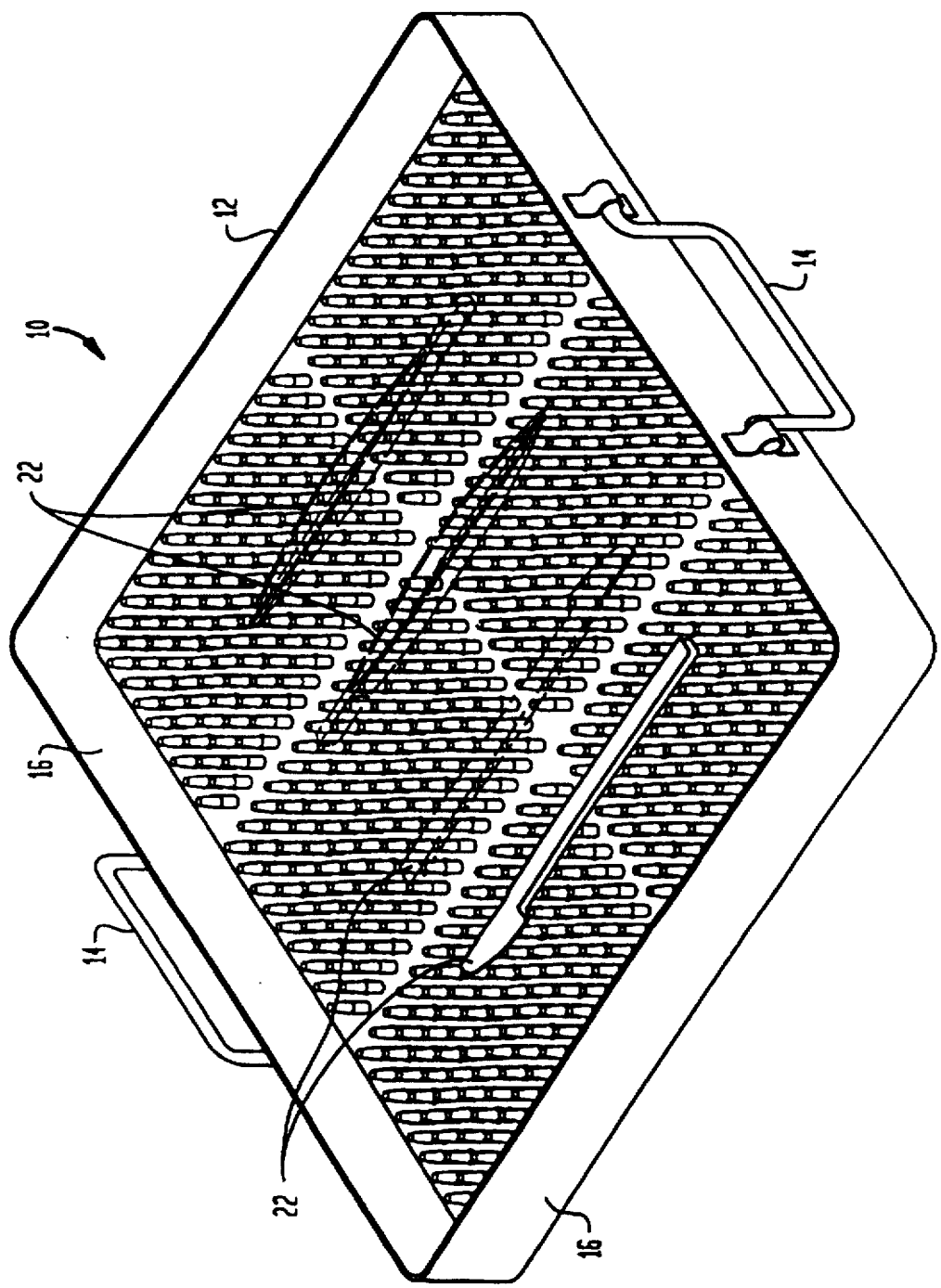
FIG. 1 is a perspective view of the preferred embodiment of the mat invention shown supporting medical instruments.

The mat invention 10 according to the preferred embodiment thereof is illustrated in FIG. 1. A conventional sterilizable tray 12 holds and supports the mat 10. Tray 12 has four sides 16 and a pair of handles 14 attached to opposite sides 16. The bottom 18 of the tray 10 includes a plurality of evenly spaced steam holes or apertures 20 arranged in a grid-like pattern. Medical instruments 22 or related tools are supported on the top surface 24 of the mat 10. The assembly is shown in an exploded perspective view in FIG. 2. It can be placed directly into a conventional steam autoclave for sterilizing purposes.

Figure 2:
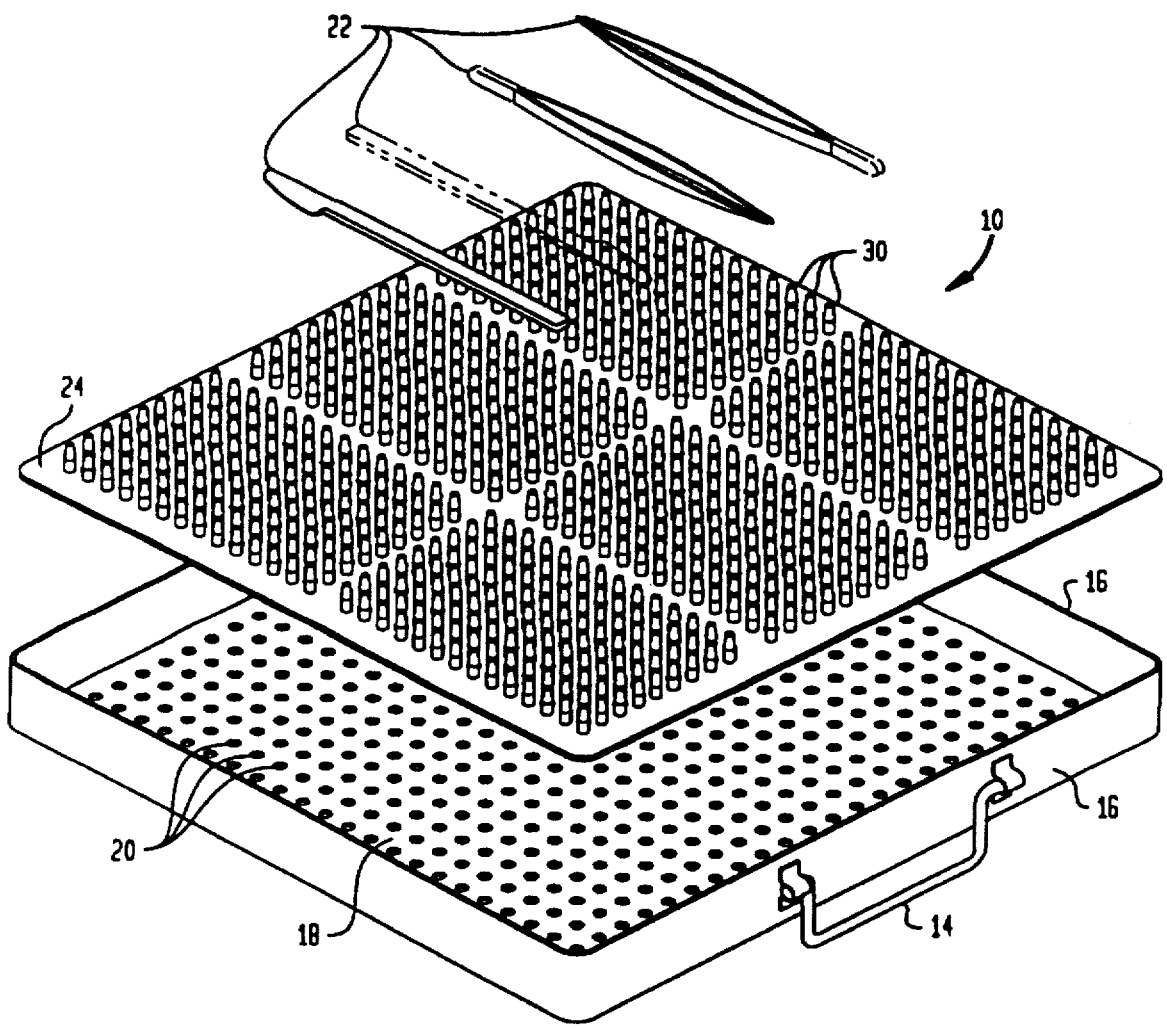
FIG. 2 is an exploded perspective view of the mat invention shown prior to its mating with a sterilizable tray.

Mat 10 has a top surface 24, as previously mentioned, a body or middle section 26, and a bottom surface 28 that faces the bottom 18 of the tray 12 when the mat 10 is in the position shown in FIGS. 1 & 2.

Top surface 24 includes a plurality of finger-like projections or bristles 30 as better seen in FIGS. 3A, 3C, 3D and 5A–5C. Each finger 30 has a cylindrical base section 32, a tapered midsection 34, and a conical top 36. The fingers 30 on the top surface 24 are resilient enough and spread out sufficiently so that instruments 22 placed on the mat 10 are supported in a floating manner.

The bottom surface 28 includes a plurality of S shaped ribs 38 that elevate the mat body 26 above the bottom 18 of the tray 12 to allow for optimum water drainage, maximum steam penetration and to reduce condensate residue to the minimum. Mat body 26 also includes a plurality of evenly spaced steam penetration holes or apertures 40. The S shaped ribs 38 separate certain adjacent steam penetration holes 46 from each other on the bottom surface 28 as seen in FIGS. 3B, 4A and 4B. A pair of nubs 42 are located at opposite ends of the S shaped ribs 38 and serve to seat and align the steam holes 20 in the bottom 18 of tray 12 with the steam penetration holes 40 in the mat body 26. The nubs 42 allow for accurate positioning of the mat 10 and the corresponding steam penetration holes 20 and 40. In this arrangement, the system allows for optimum water drainage and maximum steam penetration. Each nub 42 is smaller than the corresponding hole 20 that it occupies in the bottom 18 of tray 12 to allow for additional drainage. The nubs 42, which clearly help with mat positioning, also stop the mat 10 from sliding with respect to tray 12 and any associated case or basket during transport and use.

Figure 3D:
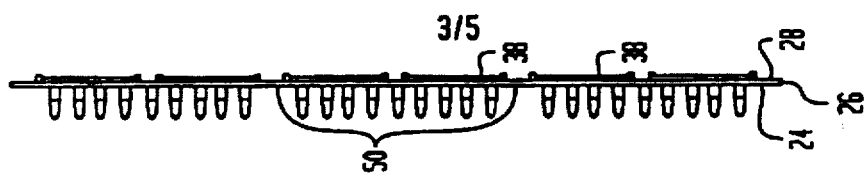
FIG. 3D is a right side elevational view of the mat invention.
Figure 3A:
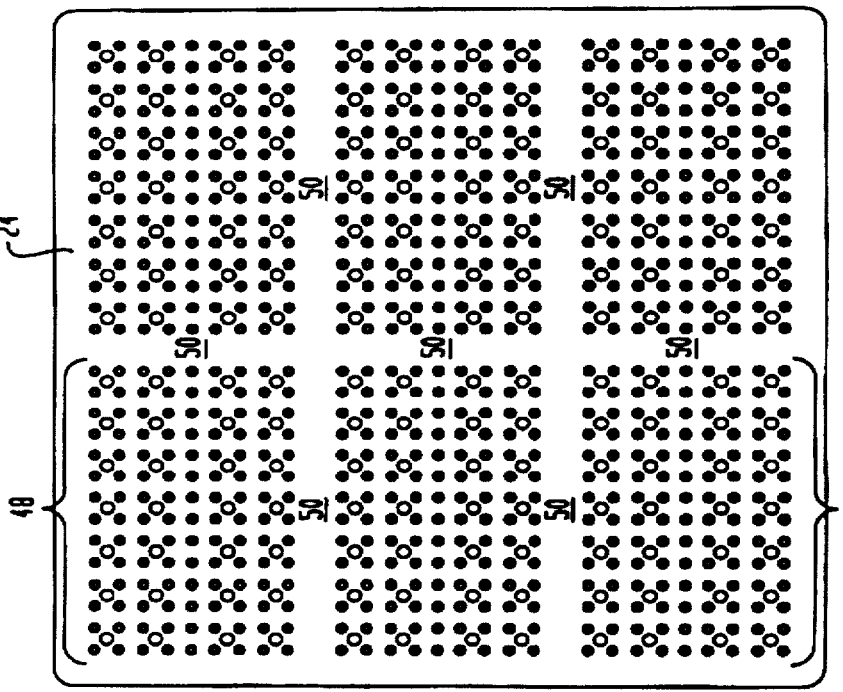
FIG. 3A is a top plan view of the mat invention.
Figure 3C:
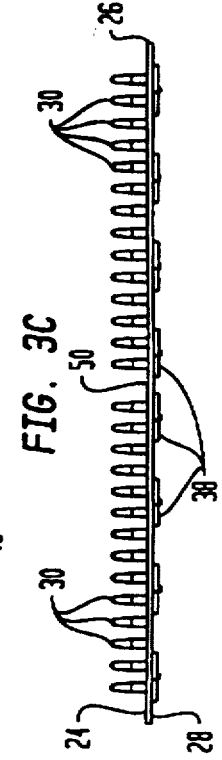
FIG. 3C is a front side elevational view of the mat invention.
Figure 3B:
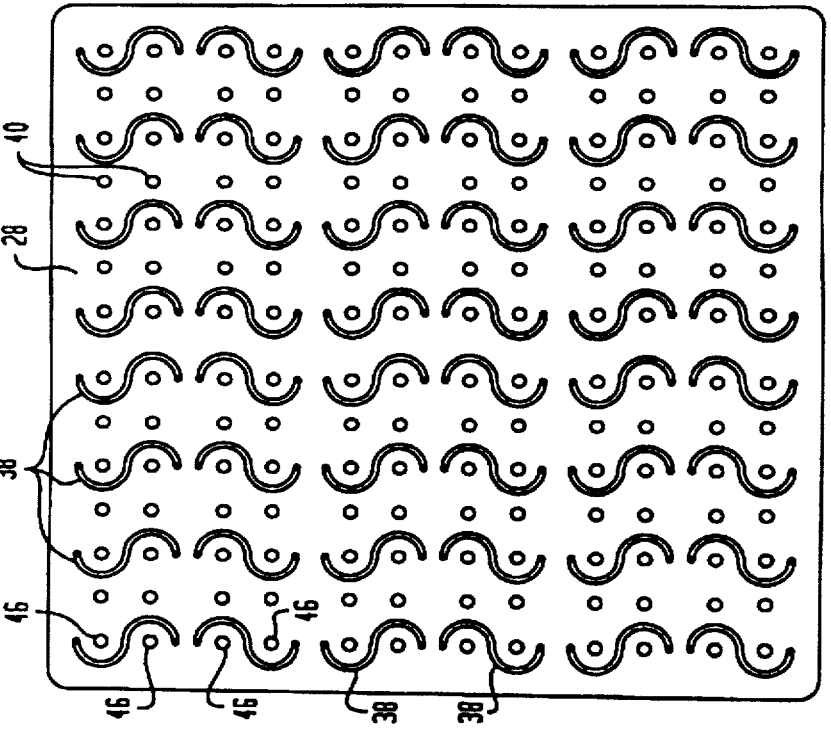
FIG. 3B is a bottom plan view of the mat invention.
Figure 4A:
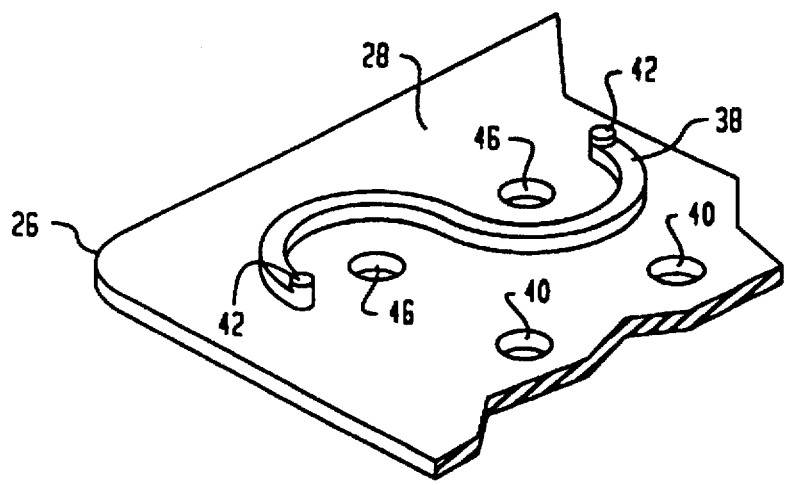
FIG. 4A is a partial, perspective bottom view of the mat illustrating a single S shaped rib and its associated positioning nubs at both ends thereof.
Figure 4B:
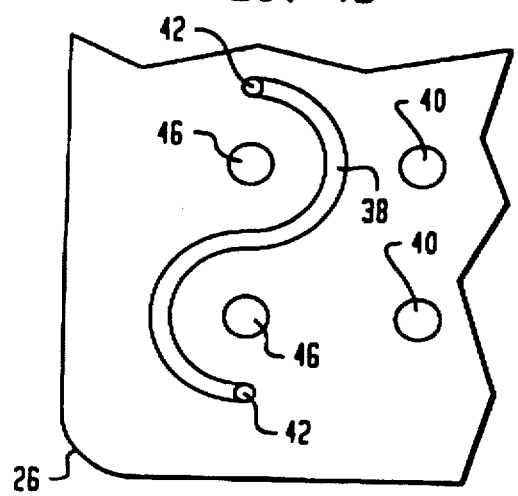
FIG. 4B is a partial, bottom plan view of the mat and associated S shaped rib structure shown in FIG. 4A.
Figure 4C:
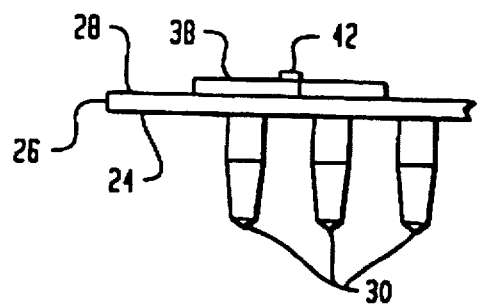
FIG. 4C is a partial, side elevational view of the mat and associated S shaped rib structure shown in FIGS. 4A and 4B.
Figure 5A:
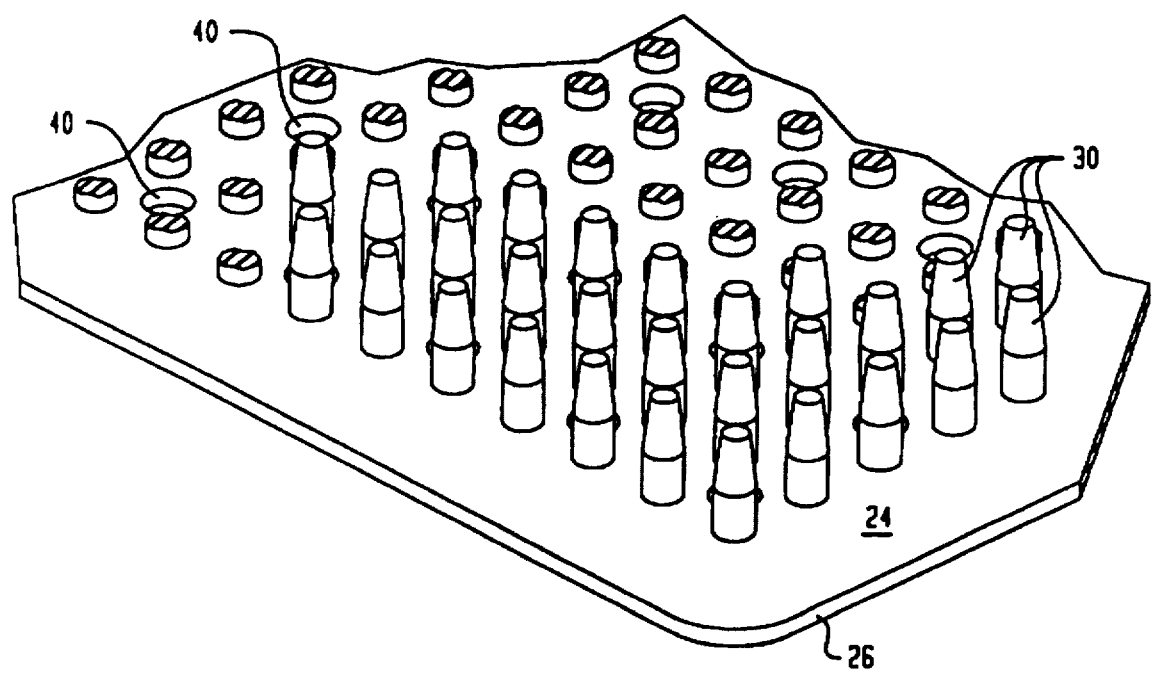
FIG. 5A is a partial, perspective top view of the mat showing the bristles or finger like instrument supports and their relationship to steam penetration holes in the body of the mat.
Figure 5B:
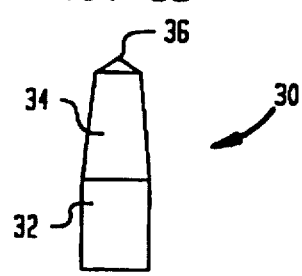
FIG. 5B is a side elevational view of a single finger like instrument support of the type shown in FIG. 5A.
Figure 5C:
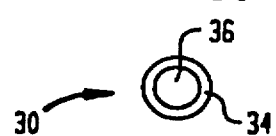
FIG. 5C is a a top plan view of the finger like instrument support shown in FIG. 5B.

The fingers or bristles 30 on the mat 10 are preferably divided up into subgroups 48 as best seen in FIGS. 3A and 3B. Subgroups 48 are separated from each other by relatively straight land areas 50. The division is visible both from the top and from the bottom. The predetermined grid pattern allows for the addition of more mat sections for larger trays or cassettes, or for the reduction of the mat 10 by cutting along the divider areas 50 of the grid pattern in which case the resulting mats 10 can be used for smaller trays 12 or smaller case systems.

The mat invention 10 just described has several advantages over sterilizable prior art mats. First, by aligning the steams holes 20 of the tray 12 with the steam penetration holes 40 of the mat 10 a significantly better sterilization takes place. Second, the small nubs 42 permit the water to drain easily from the tray. Third, the S shaped ribs 38 between adjacent holes 46 allow the steam to be directed efficiently through the mat body 26 while at the same time providing good separation between the mat body 26 and the tray bottom 18. Forth, by placing the nubs 42 at the ends of the S shaped ribs 38, the mat 10 is precisely aligned at the point where it is most critical, namely right by the steam penetration holes 20 and 40 respectively. Fifth, by placing the alignment nubs 42 directly at the ends of the S shaped ribs 38 it is not necessary to build additional structure to support and align the mat 10. In essence, the mat is both effectively separated and aligned with the same S shaped rib structure 38.

While the invention has been described with reference to the preferred embodiment thereof, it will be appreciated by those of ordinary skill in the art that modifications can be make to the structure and form of the invention without departing from the spirit and scope thereof.

What is claimed is:

1. A mat apparatus (10) used for sterilizing medical instruments (22) in a sterilizable tray (12) having a plurality of regularly spaced tray apertures (20) therein, said apparatus comprising:

a substantially flat mat body (26) having a first surface (24) and a second surface (28) located on the opposite side of said mat body (26) from said first surface (24);

at least one group of regularly space mat apertures (40) passing through said mat body (26);

a plurality of medical instruments support means (30) located on said first surface (24) for supporting medical instruments (22) during sterilization; and, solid alignment means (42) located on said second surface (28) of said mat body (26) for aligning the apertures (40) in said mat body (26) with the apertures (20) in said tray (12), said solid alignment means (42) including a plurality of aperture engaging means (42) for engaging at least some of said apertures (20) in said tray (12), said solid alignment means (42) further including a solid separation means (38) for separating said mat body (26) from said tray (12) and for connecting pairs of said aperture engaging means (42).

2. The apparatus of claim 1 wherein said aperture engaging means (42) comprise nubs (42) having a diameter less than the diameter of said apertures (20) in said tray (12).

3. The apparatus of claim 2 wherein said separation means (38) has a generally S shaped form and further wherein said S separation means (38) separates at least two adjacent apertures (46) in said mat (10) from each other.

4. The apparatus of claim 3 wherein said nubs (42) are located at the opposite ends of said S shaped separation means (38) so the said two adjacent apertures (46) separated by said S shaped separation means (38) are aligned with apertures (20) in said tray (12) so that sterilizing steam can pass efficiently through said tray (12) and said mat body (26) and contact said medical instruments (22) that lie on said first surface (24) of said mat (10).

5. The apparatus of claim 4 wherein said medical instrument support means (30) comprises a plurality of finger-like projections (30) located on first surface (24) of said mat body (26).

6. The apparatus of claim 5 wherein said apparatus includes at least two subgroups (48) of regularly spaced apertures (40) divided by straight sections (50) so that said mat (10) can be conveniently divided into a plurality of smaller mats.

7. The apparatus of claim 6 wherein a plurality of said regularly spaced apertures (40) in said mat body (26) are surrounded by four of said finger-like projections (30) arranged in a substantially square pattern.

8. A mat apparatus (10) used for sterilizing medical instruments (22) in a sterilizable tray (12) having a plurality of regularly spaced tray apertures (20) therein, said apparatus comprising:

a substantially flat mat body (26) having a first surface (24) and a second surface (28) located on the opposite side of said mat body (26) from said first surface (24);

at least one group of regularly spaced mat apertures (40) passing through said mat body (26);

a plurality of medical instruments support means (30) located on said first surface (24) for supporting medical instruments (22) during sterilization; and, solid alignment means (42) located on said second surface (28) of said mat (26) body for aligning the apertures (40) in said mat body (26) with the apertures (20) in said tray (12), said solid alignment means (42) including a plurality of aperture engaging means (42) for engaging at least some of said apertures (20) in said tray (12), said aperture engaging means (42) comprising solid nubs (42) having a diameter less than the diameter of said apertures (20) in said tray (12), said alignment means (42) further including a solid separation means (38) for separating said mat body (26) from said tray (12) and for connecting pairs of said solid nubs (42), said solid separation means (38) having a generally S shaped form and further wherein said S shaped separation means (38) separates at least two adjacent apertures (46) in said mat body (26) from each other, wherein said solid nubs (42) are located at the opposite ends of said S shaped separation means (38) so that the said two adjacent apertures (46) separated by S shaped separation means (38) are aligned with apertures (20) in said tray (12) so that sterilizing steam can pass efficiently through said tray (12) and said mat body (26) and contact said medical instruments (22) that lie on said first surface (24) of said mat apparatus (10).

* * * * *